United States Patent [19]

Kuo et al.

[11] Patent Number: 5,204,465
[45] Date of Patent: * Apr. 20, 1993

[54] PROCESS FOR THE PRODUCTION OF PIPERAZINYLPYRIMIDINE DERIVATIVES

[75] Inventors: David L. Kuo, Brig; Robert Voeffray, Basel, both of Switzerland

[73] Assignee: Lonza Ltd., Gampel/Valais, Switzerland

[ * ] Notice: The portion of the term of this patent subsequent to Apr. 6, 2010 has been disclaimed.

[21] Appl. No.: 803,067

[22] Filed: Dec. 6, 1991

[30] Foreign Application Priority Data

Dec. 18, 1990 [CH] Switzerland .......... 4015/90
Mar. 4, 1991 [CH] Switzerland .......... 639/91

[51] Int. Cl.$^5$ .......... C07D 403/04
[52] U.S. Cl. .......... 544/295
[58] Field of Search .......... 544/295

[56] References Cited

U.S. PATENT DOCUMENTS

| 4,818,756 | 4/1989 | Seidel et al. .......... 514/224.2 |
| 4,937,343 | 6/1990 | Seidel et al. .......... 544/295 |
| 4,988,809 | 1/1991 | Seidel et al. .......... 544/121 |

FOREIGN PATENT DOCUMENTS

| 0115714 | 8/1984 | European Pat. Off. . |
| 0129128 | 12/1984 | European Pat. Off. . |
| 3321969 | 12/1984 | Fed. Rep. of Germany . |
| 39680 | 4/1976 | Japan . |

OTHER PUBLICATIONS

D. J. Brown et al, The pyrimidines (1962), pp. 31–43.
D. J. Brown et al, The pyrimidines Supplement I (1970) pp. 20–24.
Hampton, Harris and Hauser, Organic Synthesis, vol. 47, (1967), pp. 92 to 96.
Tracy et al., J. Org. Chem., (1941), pp. 63 to 69.

*Primary Examiner*—Cecilia Tsang
*Attorney, Agent, or Firm*—Fisher, Christen & Sabol

[57] ABSTRACT

A process for the production of piperazinylpyrimidine derivatives of the formula:

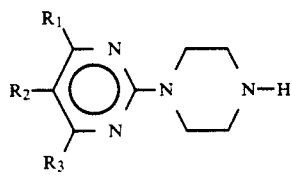

wherein $R_1$, $R_2$ and $R_3$ are the same or different and each is a hydrogen atom or a $C_1$-$C_4$ alkyl group, branched or unbranched. These piperazinylpyrimidine derivatives are acid-converted with cyanamide to an amidine salt starting from piperazine or its hydrate and then reacted with a dicarbonyl compound in the presence of a base to the end product.

19 Claims, No Drawings

PROCESS FOR THE PRODUCTION OF PIPERAZINYLPYRIMIDINE DERIVATIVES

BACKGROUND OF THE INVENTION

1. Field of the Invention

The invention relates to a process for the production of piperazinylpyrimidine derivatives of the formula:

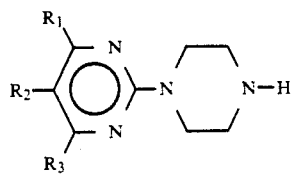
I wherein $R_1$, $R_2$ and $R_3$ are the same or different and each is a hydrogen atom or a $C_1$-$C_4$ alkyl group, branched or unbranched.

2. Background Art

The piperazinylpyrimidine derivatives of formula I are important intermediate products for the production of pharmaceutical products, such as, for the production of 4-methyl-2-piperazinylpyrimidine, which reduces the blood-sugar level [European Published Patent Application No. 0330263; West German Patent Published Application No. 3321969].

Processes for the production of piperazinylpyrimidine derivatives are described in European Published Patent Application No. 0330263. In these processes a chlorinated pyrimidine derivative is converted with a piperazine derivative to a piperazinylpyrimidine derivative. Drawbacks of these processes are that the syntheses take place over several stages and the products are obtained in poor yield.

BROAD DESCRIPTION OF THE INVENTION

The main object of this invention is to eliminate the above-described drawbacks and to make available a simple and economical process for the production of piperazinylpyrimidine derivatives. Other objects and advantages are set out herein or are obvious herefrom to one skilled in the art.

The objects and advantages of the invention are achieved by the process invention.

The invention process for the production of piperazinylpyrimidine derivatives of the formula:

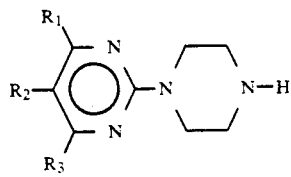
I wherein $R_1$, $R_2$ and $R_3$ are the same or different and each is a hydrogen atom or a $C_1$-$C_4$ alkyl group, branched or unbranched, is performed so that, in the first stage, piperazine or its hydrate of the formula:

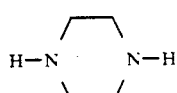
II is acid-reacted with cyanamide in a known way, according to Japanese Published Patent Application No. 51-39680, to an amidine salt of the formula:

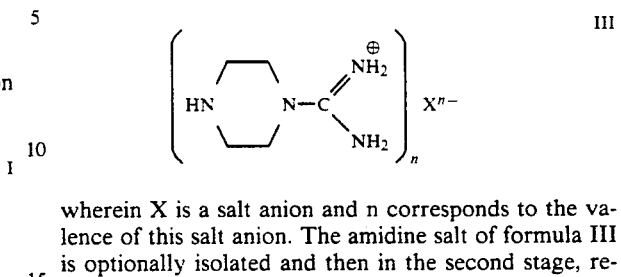
III wherein X is a salt anion and n corresponds to the valence of this salt anion. The amidine salt of formula III is optionally isolated and then in the second stage, reacted with a CH-acidic compound to the end product.

DETAILED DESCRIPTION OF THE INVENTION

Suitably, the reaction in the first stage is performed, according to Japanese Published Patent Application No. 51-39680, with 1 to 1.5 mol of cyanamide, preferably with 1.1 mol of cyanamide, relative to 1 mol of piperazine or its hydrate. Suitably, the reaction in the first stage is performed at a temperature of 40° to 60° C. Suitably, the reaction in the first stage is performed in the presence of a mineral acid. As the mineral acid, for example, sulfuric acid, hydrochloric acid or phosphoric acid can be used; consequently, $x^{n-}$ in the amidine salt then means chloride, sulfate or phosphate. In particular, concentrated sulfuric acid is used as the mineral acid. Preferably, the mineral acid and the piperazine or its hydrate are used in equimolar amounts in the first stage.

After a usual reaction time of 1 to 2 hours, the amidine salt is then optionally obtained according to usual working-up methods, e.g., by concentration by evaporation, or the entire reaction mixture is used directly for the second stage.

The second stage, the reaction of the amidine salt to the end product, takes place with a CH-acidic compound. Suitable representatives of the CH-acidic compounds are:

dicarbonyl compounds of the formula:

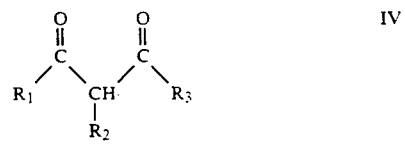
IV wherein $R_1$, $R_2$ and $R_3$ are the same or different and each is a hydrogen atom or a $C_1$-$C_4$ alkyl group, branched or unbranched, or tetra ($C_1$-$C_4$) alkoxy propanes of the formula:

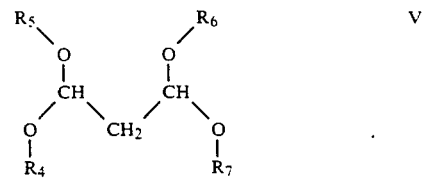
V wherein $R_4$, $R_5$, and $R_6$ and $R_7$ each is a $C_1$-$C_4$ alkyl group, branched or unbranched.

Reaction With a Dicarbonyl Compound of Formula IV

Preferred compounds of formula IV are:

2,4-octanedione ($R_1$=butyl, $R_2$=H, $R_3$=methyl),
acetylacetone ($R_1$=methyl, $R_2$=H, $R_3$=methyl),
3-methyl-2,4-pentanedion ($R_1$=$R_2$=$R_3$=methyl), and
4-hydroxy-3-methyl-3-buten-2-one ($R_1$=$R_2$=methyl, $R_3$=H).

The production of 2,4-octanedione as a representative of the compounds of formula IV takes place, starting from acetylacetone, by reaction with sodium, liquid ammonia and propyl bromide [Hampton, Harris and Hauser, Org. Synthesis, Vol. 47, (1967), pages 92 to 96] and the production of 4-hydroxy-3-methyl-3-buten-2-one as a representative of formula IV takes place by reaction of 2-butanone with methyl formate and metallic sodium [Tracy et al., J. Org. Chem., (1941), pages 63 to ]. The usual dicarbonyl compounds can be obtained commercially.

Suitably, the reaction with the CH-acidic compound of formula IV (dicarbonyl compound) in the second stage is performed with 0.5 to 3 mol of dicarbonyl compound, preferably with 0.5 to 2 mol, relative to 1 mol of amidine salt, at a suitable temperature of 20° to 100° C., preferably at a temperature of 65° to 80° C. Suitably, the reaction with the CH-acidic compound of formula IV in the second stage is performed in a polar solvent. As the polar solvent, low-boiling alcohols, such as, methanol, ethanol or propanol can be used. Preferably, methanol is used as the solvent. The reaction in the second stage, which is performed with the CH-acidic compound of formula IV, is performed in the presence of a base. As the base, an alcoholate, such as, sodium methanolate, sodium ethanolate, sodium propanolate, sodium butanolate or potassium-tert-butanolate, can be used. Preferably, sodium methanolate is used. Preferably, the base is used in an amount of 1 to 4 mol, relative to 1 mol of dicarbonyl compound.

After a usual reaction time of 2 to 10 hours, the end product is then isolated according to usual working-up methods, e.g., by extraction or column chromatography.

Reaction With Tetra($C_1$-$C_4$)alkoxypropane of Formula V

As a preferred representative of formula V, tetramethoxypropane is used.

Suitably, the reaction in the second stage is performed with 0.25 to 2 moles of tetra($C_1$-$C_4$)alkoxypropane, preferably with 1 mol, relative to 1 mol of amidine salt, at a suitable temperature of 20° to 100° C., preferably at a temperature of 60° to 80° C. Suitably, the reaction in the second stage is performed with tetra($C_1$-$C_4$)alkoxypropane in the presence of an aqueous mineral acid. As the mineral acid, for example, sulfuric acid, hydrochloric acid or phosphoric acid can be used. Suitably, a 30 to 60 percent mineral acid is used as an aqueous mineral acid. The aqueous mineral acid can be used in an amount of 4 to 10 moles, relative to 1 mol of tetra($C_1$-$C_4$)alkoxypropane. Preferably, a 30 to 60 percent sulfuric acid in an amount of 4 to 10 moles, relative to 1 mol of tetra($C_1$-$C_4$)alkoxypropane, is used.

After a usual reaction time of 1 to 24 hours, the end product is then obtained according to usual working-up methods, e.g., by extraction and subsequent distillation.

Preferably, the entire reaction is performed in a one-pot process to the end product.

Preferably, 2-(1-piperazinyl)pyrimidine, 6-(1-butyl)-4-methyl-2-(1-piperazinyl)pyrimidine, 4,6-dimethyl-2-(1-piperazinyl)pyrimidine, 4,5-dimethyl-2-(1-piperazinyl)-pyrimidine and 4,5,6-trimethyl-2-(1-piperazinyl)pyrimidine are obtained as end products.

The piperazinylpyrimidine derivatives can be converted, for example, with methyl iodide or isopropyl bromide to the corresponding alkylated piperazinyl-pyrimidine derivatives (European Patent Application No. 115,714), which, as initially mentioned, are important intermediate products of pharmaceutical products, such as, 4-methyl-2-piperazinylpyrimidine, for reducing the blood-sugar level.

EXAMPLE 1

Production of 2,4-octanedione (Not According To The Invention)

Metallic sodium (0.3 g, 13 mmol) was added to a liquid ammonia solution (400 ml). After the mixture was dyed blue, iron nitrate hydrate (0.13 g, 0.3 mmol) was added and then again metallic sodium (12.6 g, 0.55 mol) was added. After completion of the $NaNH_2$ formation, a solution of acetylacetone (30 g, 299 mmol) in ethyl ether (20 ml) was added within 10 minutes at −78° C. After 20 minutes, propyl bromide (28.2 g, 299.6 mmol) was added by instillation within 25 minutes. After further stirring for 50 minutes, ethyl ether (100 ml) was added and the ammonia was evaporated. After about 12 hours, the mixture was extracted with ethyl ether 3 times (50 ml each) and the combined organic phases were washed twice with an NaCl solution (50 ml each) and dried on $Na_2SO_4$. After removal of the solvent, 33 g of 2,4-octanedion was obtained. After vacuum distillation (13.5 mbars, 78° C.), 22.59 g of 2,4-octanedion, corresponding to a yield of 52.9 percent, was obtained as a colorless oil.

EXAMPLE 2

Production of 4-hydroxy-3-methyl-3-buten-2-one (Not According To The Invention)

Metallic sodium (15.87 g, 0.69 mol) was added in a period of 4 hours to a solution of 2-butanone (50 g, 0.69 mol) and methyl formate (41.9 g, 0.69 mol) in diethyl ether at 0.C. The resultant yellow mixture was stirred for 14 hours at 20.C. The formed sodium salt was filtered and washed with previously-dried diethyl ether. Then, the sodium salt was dissolved in cold $H_2O$ and the dark red liquid was acidified with 25 percent sulfuric acid (150 ml) up to a pH of about 3.7. Then, it was extracted 5 times with ethyl ether (100 ml), the combined organic phases were washed once with $H_2O$ (50 ml) and once with NaCl solution (50 ml) and then dried on $Na_2SO_4$. After removal of the solvent in a vacuum, 39.59 g of 4-hydroxy-3-methyl-3-buten-2-one, corresponding to a yield of 57 percent, was obtained.

EXAMPLE 3

Production of 2-(1-piperazinyl)-amidino sulfate 95.6 percent sulfuric acid (74.5 g, 0.72 mol) wa added to piperazine hexahydrate (552 g, 2.78 mol) within 10 minutes. This mixture was heated to 50° C. and then a 25 percent aqueous solution of cyanamide (484 g, 2.88 mol) wa slowly instilled within 2 hours. After further stirring for 2 hours at 50° C., 95.6 percent sulfuric acid (0.47 mol) was added within 10 minutes and all of this was heated to 63° C. Then, the mixture was evaporated to dryness and absolute methanol (800 ml) was added to this sticky mass (601 g) and cooled for 1 hour. Then, the solution was filtered, washed twice with cold absolute methanol (100 ml). After drying in a vacuum, 328 g of 2-(1-piperazinyl)-amidino sulfate, corresponding to a yield of 77.3 percent, was obtained. The mother liquor was cooled for 2 days, then filtered, washed twice with absolute methanol (50 ml) and dried under a vacuum. 43.3 g of 2-(1-piperazinyl)amidino sulfate, corresponding to a yield of 10.2 percent, was obtained. After combining these two fractions, the total yield was 87.6 percent, relative to the initial product.

EXAMPLE 4

Process for the Production of 2-(1-piperazinyl)pyrimidine 50 percent sulfuric acid (21.5 g, 109.5 mmol) was added to 2-(1-piperazinyl)-amidino sulfate (5.2 g, 14.6 mmol) and the mixture was heated to 70° C. Then, tetramethoxypropane (2.47 ml, 14.6 mmol) was slowly added within 2 hours. After 5 hours at 70° C., the mixture was cooled overnight to 20° C. Then, $H_2O$ (20 ml) and $CH_2Cl_2$ (40 ml) were added to 0° C., and the pH of the solution was adjusted to pH 14 with 20 percent NaOH (50 ml). The mixture was extracted 5 times with $CH_2Cl_2$ (50 ml) and the combined organic phases were dried on $Na_2SO_4$. The solvent was evaporated in a vacuum, and 2.08 g of crude product, corresponding to a yield of 86.6 percent, was obtained. After distillation at 150° to 175° C. (0.5 mbar), 1.37 g of product, corresponding to a yield of 57 percent, relative to the amidino sulfate used, was obtained.

EXAMPLE 5

Production of 6-(1-butyl)-4-methyl-2-(1-piperazinyl)pyrimidine

Sodium methanolate (12.1 ml, 63.4 mmol) was added to a solution of 2-(1-piperazinyl)amidino sulfate (10.5 g, 29.6 mmol) in absolute methanol (20 ml). The mixture was refluxed for 10 minutes at 80° C. Then, 2,4-octanedion (3.0 g, 21.1 mmol) was added within 1.5 hours. After completion of the reaction, the mixture was stirred for 12 hours at 80° C., cooled and then extracted 5 times with $CHCl_3$ (20 ml). Then, the combined organic phases was washed once with $H_2O$ (20 ml) and dried on $Na_2SO_4$. After removal of the solvent in a vacuum, a residue of 2.5 g was obtained, and after distillation (0° to 180° C., 0.5 mbar), 2.1 g of product, corresponding to a yield of 42 percent, relative to the amidino sulfate used, was obtained as a colorless oil.

EXAMPLE 6

Production of 4,6-dimethyl-2-(1-piperazinyl)pyrimidine

Sodium methanolate 10.6 g, 58 8 mmol) was added to a solution of 2-(1-piperazinyl)amidino sulfate (10 g, 28.2 mol) in absolute methanol (20 ml). The mixture was refluxed for 10 minutes at 80° C. Then, acetylacetone (2.35 g, 23.5 mmol) was added within 70 minutes. After completion of the reaction, the mixture was stirred for 15 hours at 80° C., cooled and then extracted 4 times with $CHCl_3$ (25 ml). Then, the combined organic phases were washed once with $H_2O$ (20 ml) and dried on $Na_2SO_4$. After removal of the solvent in a vacuum, the residue (3.1 g) was distilled (110° to 205° C., 0.49 mbar) and 2.22 g of product, corresponding to a yield of 49 percent, relative to the amidino sulfate used, was obtained as a colorless oil.

EXAMPLE 7

Production of 4,5-dimethyl-2-(1-piperazinyl)pyrimidine

Sodium methanolate (11.1, 60 mmol) was added to a solution of 2-(1-piperazinyl)amidino sulfate (7 g, 20 mmol) in absolute methanol (15 ml). The mixture was refluxed for 10 minutes to 80° C. Then, 4-hydroxy-3-methyl-3-buten-2-one (2 g, 20 mmol) was added over a period of 1.5 hours. After completion of the reaction, the mixture was stirred for another 6 hours at 80° C., cooled and then extracted 5 times with $CHCl_3$ (20 ml). The combined organic phases were washed twice with water (50 ml) and dried on $Na_2SO_4$. After removal of the solvent in a vacuum, 1.39 g of residue was obtained. The latter was purified by column chromatography [filled with silica gel, (Fluka, 230-440 mesh) and methanol/dichloromethane in a 5:1 ratio as mobile solvent]. Then, 0.5 g of 4,5-dimethyl-3-(1-piperazinyl)-pyrimidine, corresponding to a yield of 13 percent, relative to the amidino sulfate used, was obtained as a colorless oil.

EXAMPLE 8

Production of 4,5,6-trimethyl-2-(1-piperazinyl)pyrimidine

Sodium methanolate (14.6 g, 78.9 mmol) was added to a solution of 2-(1-piperazinyl)amidino sulfate (11.2 g, 31.6 mmol) in absolute methanol (20 ml). The mixture was refluxed for 20 minutes to 80° C. and then 3-methyl-2,4-pentanedion (3 g, 26.3 mmol) was added over a period of 2.5 hours. After completion of the reaction, the mixture was stirred for another 3 hours at 80° C., cooled and then extracted 5 times with $CHCl_3$ (20 ml). The combined organic phases were washed once with $H_2O$ (20 ml) and dried on $Na_2SO_4$. After removal of the solvent in a vacuum, a light brown residue (2.2 g) was obtained, which was purified by column chromatography [silica gel, (Fluka 220-440 mesh) and methanol/dichloromethane in a 5:1 ratio as a mobile solvent]. 1.99 g of 4,5,6-trimethyl-2-(1-piperazinyl)pyrimidine, corresponding to a yield of 35 percent, relative to the amidino sulfate used, was obtained as a colorless oil.

EXAMPLE 9

Production of 4-methyl-2-[1-(4-methylpiperazinyl)]pyrimidine (Not According To The Invention)

Sodium hydride (0.4 g, 13.5 mmol) was added to a solution of 4-methyl-2-(1-piperazinyl)pyrimidine (2.0 g, 11.2 mmol) in dried dimethylformamide (15 ml) under argon atmosphere. The mixture was stirred for another 55 minutes at 20° C. and then methyl iodide (1.75 g, 12.4 mmol) was added by instillation within 10 minutes. The mixture was stirred for another 1.5 hours, then $H_2O$ (5 ml) was carefully added. After 20 minutes, the mixture was extracted three times with $CH_2Cl_2$ (15 ml), the combined organic phases were washed once with $H_2O$ (20 ml), and then dried on sodium sulfate. After removal of the solvent in a vacuum, 2.1 g of yellow oil was obtained, which was purified by column chromatography (silica gel, mobile solvent: methanol/dichloromethane in a 1:1 ratio). 1.53 g of 4-methyl-2-[1-(4-methylpiperazinyl)]pyrimidine, corresponding to a yield of 71.2 percent, relative to the 4-methyl-2-(1-piperazinyl)-pyrimidine used, was obtained as a yellow oil.

What is claimed is:

1. Process for the production of a piperazinylpyrimidine compound of the formula:

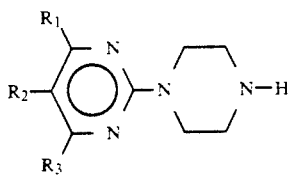

I wherein $R_1$, $R_2$ and $R_3$ are the same or different and each is a hydrogen atom or a $C_1$-$C_4$ alkyl group, branched or unbranched, characterized in that, in a first stage, piperazine of the formula:

II or its hydrate is acid-reacted with cyanamide to an amidine salt of the formula:

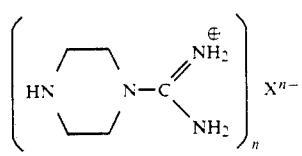

III wherein X is an anion which forms said amidine salt and n corresponds to the valence of said anion which forms said amidine salt, the amidine salt of formula III is optionally isolated, and then, in a second stage, the amidine salt of formula III is reacted with a CH-acidic compound to said piperazinylpyrimidine compound of formula I.

2. Process according to claim 1 wherein the reaction in the first stage is performed with 1 and 1.5 moles of cyanamide, relative to 1 mol of piperazine.

3. Process according to claim 2 wherein the reaction in the first stage is performed in the presence of a mineral acid.

4. Process according to claim 3 wherein the reaction in the first stage is performed at a temperature of 40° to 60° C.

5. Process according to claim 4 wherein, in the second stage, a dicarbonyl compound of the formula:

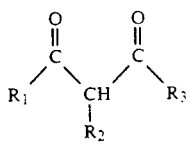

IV wherein $R_1$, $R_2$ and $R_3$ are the same or different and each is a hydrogen atom or a $C_1$-$C_4$ alkyl group, branched or unbranched, is used as the CH-acidic compound, in the second stage, the reaction is performed at a temperature of 20° to 100° C., in the second stage, the reaction with a dicarbonyl compound, is performed in the presence of a base in a polar solvent, the polar solvent being a low-boiling alcohol, and the case being an alcoholate.

6. Process according to claim 4 wherein, in the second stage, a tetra($C_1$-$C_4$)alkoxypropane of the formula:

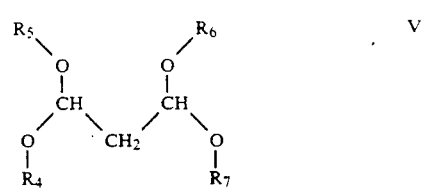

V wherein $R_4$, $R_5$, $R_6$ and $R_7$ are the same or different and each is a $C_1$-$C_4$ alkyl group, branched or unbranched, is used as the CH-acidic compound, and, in the second stage, the reaction is performed in the presence of an aqueous mineral acid.

7. Process according to claim 5 wherein, in the second stage, 2,4-octanedione, acetylacetone, 3-methyl-2,4-pentanedion or 4-hydroxy-3-methyl-3-buten-2-one is used as the dicarbonyl compound.

8. Process according to claim 6 wherein, in the second stage, tetramethoxypropane is used as the tetra($C_1$-$C_4$)alkoxypropane.

9. Process according to claim 1 wherein the reaction in the first stage is performed in the presence of a mineral acid.

10. Process according to claim 1 wherein the reaction in the first stage is performed at a temperature of 40° to 60° C.

11. Process according to claim 1 wherein, in the second stage, a dicarbonyl compound of the formula:

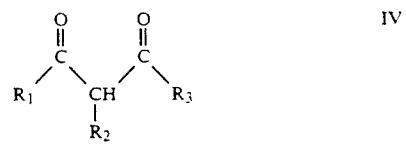

IV wherein $R_1$, $R_2$ and $R_3$ are the same or different and each is a hydrogen atom or a $C_1$-$C_4$ alkyl group, branched or unbranched, is used as the CH-acidic compound, in the second step, the reaction is performed at a temperature of 20° to 100° C., and, in the second stage, the reaction with a dicarbonyl compound, is performed in the presence of a base in a polar solvent, the polar solvent being a low-boiling alcohol, and the base being an alcoholate.

12. Process according to claim 1 wherein, in the second stage, a tetra($C_1$-$C_4$)alkoxypropane of the formula:

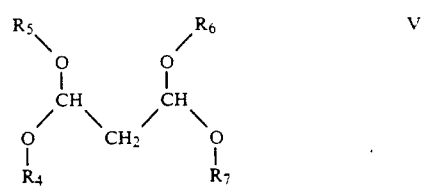

V wherein $R_4$, $R_5$, and $R_6$ and $R_7$ are the same or different and each is a $C_1$-$C_4$ alkyl group, branched or unbranched, is used as the CH-acidic compound, and, in the second stage, the reaction is performed in the presence of an aqueous mineral acid.

13. Process according to claim 6 wherein, in the second stage, the mineral acid is sulfuric acid, hydrochloric acid or phosphoric acid.

14. Process according to claim 12 wherein, in the second stage, the mineral acid is sulfuric acid, hydrochloric acid or phosphoric acid.

15. Process according to claim 5 wherein, in the second stage, the alcoholate is sodium methanolate, sodium ethanolate, sodium propanolate, sodium butanolate or potassium-tertbutanolate, and the low-boiling alcohol is methanol, ethanol or propanol.

16. Process according to claim 11 wherein, in the second stage, the alcoholate is sodium methanolate, sodium ethanolate, sodium propanolate, sodium butanolate or potassium-tertbutanolate, and the low-boiling alcohol is methanol, ethanol or propanol.

17. Process according to claim 1 wherein $X^{n-}$ is chloride, sulfate or phosphate.

18. Process according to claim 1 wherein $R_1$, $R_2$ and $R_3$ are hydrogen.

19. Process according to claim 1 wherein $R_1$, $R_2$ and $R_3$ are $C_1$–$C_4$ alkoxy groups.

* * * * *